United States Patent [19]

De Clercq et al.

[11] Patent Number: 4,548,819
[45] Date of Patent: Oct. 22, 1985

[54] DERIVATIVES OF 9-(2-HYDROXYETHOXYMETHYL) GUANINE

[76] Inventors: Erik D. A. De Clercq, Lebrunstraat 35-7, 3000 Leuven; Hubert J. H. E. Vander Haeghe, Prediktherenberg 28, 3009 Winksele; Roger H. C. Busson, Kapelstraat 67,, 3110 Rotselaar, all of Belgium

[21] Appl. No.: 507,712

[22] Filed: Jun. 23, 1983

[30] Foreign Application Priority Data

Jun. 29, 1985 [NL] Netherlands ............... 8202626

[51] Int. Cl.$^4$ ................. C07D 473/18; A61K 31/52
[52] U.S. Cl. ................... 514/261; 544/276; 544,277; 514/931
[58] Field of Search .......... 424/253; 544/276, 277

[56] References Cited

U.S. PATENT DOCUMENTS 4,323,573  4/1982  Schaeffer ............... 544/276

OTHER PUBLICATIONS

Kaufman et al., Antimicrobial Agents and Chemotherapy, vol. 14, No. 6, pp. 842–845 (1978).
Maudgal et al., Arch. Ophthalmol., vol. 102, pp. 140–142 (1984).

Primary Examiner—Nicholas S. Rizzo
Attorney, Agent, or Firm—Donald Brown

[57] ABSTRACT

Compounds of the general formula

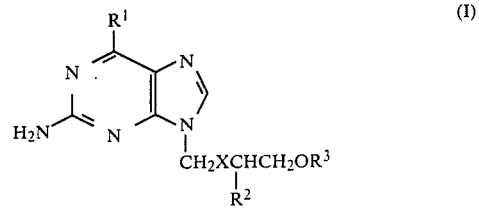

(wherein X represents an oxygen or sulphur atom, $R^1$ represents a hydroxy or amino group, $R^2$ represents a hydrogen atom or a group of formula —$CH_2OR^3{}_a$ and $R^3$ and $R^3{}_a$ which may be the same or different, each represents an amino acid acyl radical) and physiologically acceptable salts thereof are useful for the treatment of viral infections and have been found to have a surprisingly high water-solubility which renders them of value in the formulation of aqueous pharmaceutical preparations. Processes for preparing the compounds are described.

8 Claims, No Drawings

DERIVATIVES OF 9-(2-HYDROXYETHOXYMETHYL) GUANINE

The invention relates to new esters of 9-(2-hydroxyethoxymethyl)guanine having valuable antiviral properties.

9-(2-Hydroxyethoxymethyl)guanine, otherwise known as acyclovir, possesses a potential antiviral activity, particularly against herpes viruses (H. J. Schaeffer et al, "Nature", 272, 583–585 (1978)). In certain applications, acyclovir suffers from the disadvantage that it has only a limited solubility in water, namely 1.23 mg/ml at 25° C. This relatively low solubility may limit the formulation of the drug in aqueous pharmaceutical preparations where some solubilisation of the drug is required.

We have now discovered that certain ester derivatives of acyclovir, as described below, surprisingly have an improved water-solubility compared with acyclovir which enables the derivatives to be used to a greater extent than acyclovir in the formulation of aqueous preparations. According to one feature of the present invention we provide compounds of the general formula

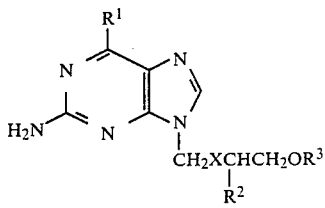

(I)

(wherein X represents an oxygen or sulphur atom, $R^1$ represents a hydroxy or amino group, $R^2$ represents a hydrogen atom or a group of formula —$CH_2OR^3{}_a$ and $R^3$ and $R^3{}_a$ which may be the same or different, each represents an amino acid acyl radical) and physiologically acceptable salts thereof.

The improved water-solubility of the compounds according to the invention is particularly marked in regard to the specified salts of the compounds of formula (I). Thus, for example, the compounds described in Examples 1 to 3 below have been found to have a water-solubility of up to about 6%, determined in an isotonic phosphate buffer at pH 7. The compounds according to the invention are thus particularly useful for the formulation of aqueous pharmaceutical preparations such as eye drops and injectable preparations for intramuscular administration.

In addition to their relatively high water-solubility, the compounds according to the invention possess substantially the same antiviral effect as acyclovir in vitro. The advantageous increase in water-solubility of the compounds is thus not gained at the expense of antiviral potency. Indeed, it has been found that in certain clinical applications, e.g. the treatment of stromal keratitis, the esters may provide a superior therapeutic effect to acyclovir.

Preferred compounds according to the invention include those wherein $R^1$ represents a hydroxy group, $R^2$ represents a hydrogen atom and X represents an oxygen atom, i.e. amino acid esters of acyclovir, and their pharmacologically acceptable salts.

With regard to the amino acid acyl radical(s) represented by $R^3$ and/or $R^3{}_a$, such radicals are preferably derived from an aliphatic amino acid, eg, glycine, α- or β alanine.

The pharmacologically acceptable salts of the compounds of formula (I) are preferably acid addition salts derived from an appropriate acid, e.g. hydrochloric, sulphuric, phosphoric, maleic, fumaric, citric, tartaric, lactic or acetic acid.

The compounds according to the invention may be prepared in conventional manner, e.g. by a process as described below.

Thus, according to a further feature of the present invention we provide a process for the preparation of compounds of general formula (I) above and pharmacologically acceptable salts thereof which comprises (a) reacting a compound of formula

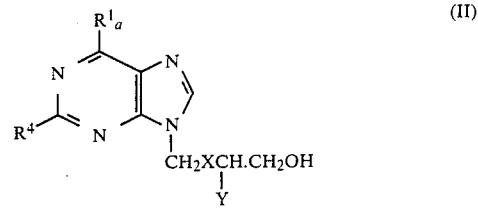

(II)

(wherein X is as defined above, $R^1{}_a$ is an optionally protected hydroxy or amino group, $R^4$ is an optionally protected amino group and Y represents a hydrogen atom or a hydroxymethyl group) with an optionally protected amino acid or a functional equivalent thereof;

(b) converting a compound of formula

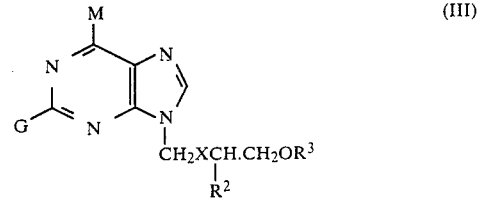

(III)

(wherein X, $R^2$ and $R^3$ are as defined above; and M represents a hydroxy or amino group and G represents an atom or group that can be replaced by or converted to an amino group; or G represents an amino group and M represents an atom or group that can be replaced by or converted to an amino or hydroxy group) into a compound of formula (I) or a pharmacologically acceptable salt thereof; or (c) reacting a compound of formula

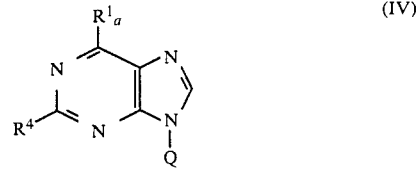

(IV)

(wherein $R^1{}_a$ and $R^4$ are as defined above and Q represents a leaving atom or group) with a compound of formula

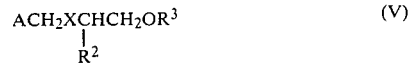

(V)

(wherein X, $R^2$ and $R^3$ are as defined above and A represents a leaving group or atom); and optionally effecting one or more of the following conversions, in any desired sequence:

(i) removal of any protecting groups;

(ii) where the resulting product is a compound of formula (I), conversion of the said compound into a pharmacologically acceptable salt thereof; and (iii) where the resulting product is a pharmacologically acceptable salt of a compound of formula (I), conversion of the said salt into the parent compound.

With regard to process (a), the esterification reaction may be carried out in conventional manner, for example in a solvent such as pyridine, dimethylformamide etc, in the presence of an acid acceptor such as triethylamine or N,N'-dicyclohexyl-carbodiimide, optionally in the presence of an acidic catalyst such as p-toluene sulphonic acid. The water formed during the reaction may, if desired, be removed in conventional manner, for example by distillation or by the addition of a water-binding substance. Subsequently, the ester obtained as reaction product may be isolated in conventional manner. As an alternative to the use of the appropriate amino acid per se, a functional equivalent of such an acid may be employed, e.g. an acid halide such as the acid chloride, or an acid anhydride.

In order to avoid undesirable side-reactions, it may be advantageous to use an amino-protected derivative, examples of preferred amino-protecting groups including acyl, e.g. $C_{1-4}$alkanoyl such as acetyl; aryloxycarbonyl, e.g. benzyloxy carbonyl; and azido groups.

Conversion of a compound of formula (III) into a compound of formula (I), by method (b), can be achieved by various means. For example M and/or G may each represent an azide group which can be reduced to an amino group by catalytic hydrogenation using a suitable catalyst such as palladium. Alternatively, M and/or G may each represent a halogen atom or an alkylthio or alkylsulphonyl group which can be converted to a amino group by aminolysis using for example ammonia. For the preparation of the compound of formula (I) wherein $R^1$ is a hydroxy group, a compound of formula (III) wherein M is an amino group may be converted for example by treatment with nitrous acid. Alternatively, a compound of formula (III) wherein M is a mercapto or alkylthio group may be converted into a compound of formula (I) wherein $R^1$ is a hydroxy group by oxidation and hydrolysis in conventional manner. Also, a compound of formula (III) wherein M is halogen can be converted into a compound of formula (I) wherein $R^1$ is hydroxy by treatment with 2-mercaptoethanol and an alkali metal alkoxide, e.g. sodium methoxide.

These processes together with other conventional processes are described in Fused Pyrimidines, Part II, Purines, Ed. by D. J. Brown (1971), Wiley-Interscience. In a further alternative a compound of formula (III) wherein M is an amino group may be converted into a compound of formula (I) wherein $R^1$ is a hydroxy group by treatment with a deaminating enzyme such as adenosine deaminase.

In process (c), the group Q in formula (IV) may for example represent a hydrogen atom; an acyl group, e.g. a $C_{1-4}$alkanoyl group such as an acetyl group or an aroyl group such an a benzoyl group; or a tri-$C_{1-4}$alkylsilyl group such as a trimethylsilyl group. The group A in formula (V) may for example represent a halogen atom (e.g. chlorine) or an acyloxy group wherein the acyl moiety may be for example a $C_{1-4}$alkanoyl group such as acetyl or an aroyl group such as benzoyl. The reaction may be conveniently effected in a strong polar solvent such as dimethylformamide or hexamethylphosphoramide, advantageously in the presence of a base such as triethylamine or potassium carbonate. Alternatively, a thermal condensation may be effected by heating the compounds of formulae (IV) and (V) in the presence of a catalytic amount of a strong acid, e.g. sulphuric acid.

Compounds of formulae (II) to (VIII) employed as intermediates in the synthesis of the compounds of formula (I) can be prepared in conventional manner, e.g. by procedures described in U.K. Patent Specification No. 1523865. These methods rely on intermediates prepared from simply substituted purines, which may be available commercially, or prepared according to techniques which are well known per se and which are disclosed in the literature such as the aforementioned text-book. Thus, for example, compounds of formula (III) may be generally prepared by using an analogous procedure to that of process (c), i.e. reacting an appropriate purine with a compound of formula (V).

The optional conversions (i), (ii) and (iii) may be effected in conventional manner. Thus, for example, removal of protecting groups in conversion (i) may be effected by hydrolysis, solvolysis or hydrogenolysis as appropriate. With regard to removal of protecting groups on the amino acid acyl radicals, hydrogenolysis, e.g. of aryloxycarbonyl protecting groups, and conversion of azido group, e.g. by catalytic hydrogenation, e.g. using a palladium catalyst, are preferred. With regard to protection of the groups in the 2- and/or 6-positions of purine nucleus, these may be selected for example from acyl groups such as $C_{1-4}$ alkanoyl groups e.g. acetyl, aroyl groups, e.g. benzoyl; arylmethyl groups e.g. benzyl; or tri-$C_{1-4}$alkylsilyl e.g. trimethylsilyl. Arylmethyl blocking groups, may be removed for example by hydrogenolysis, e.g. by hydrogenation in the presence of Raney nickel or a palladium catalyst or by the use of sodium in liquid ammonia. Acyl blocking groups may be removed for example by hydrolysis using for example an amine such as methylamine or triethylamine, advantageously in an aqueous medium. Trialkylsilyl blocking groups may be removed for example by solvolysis e.g. with alcoholic or aqueous ammonia, or by alcoholysis.

The conversion of a compound of formula (I) into a pharmacologically acceptable salt may be effected in conventional manner, e.g. by treatment of the compound with an appropriate acid to form an acid addition salt. Similarly, conversion of a salt into the parent compound of formula (I) may be effected in conventional manner.

The present invention also provides compounds of formula (I) and pharmacologically acceptable salts thereof (hereinafter identified as "the active compounds") for use in the treatment or prophylaxis of a viral disease in an animal, e.g. a mammal such as man. The compounds are especially useful for the treatment or prophylaxis of diseases caused by various DNA viruses, such as herpes infections, for example herpes simplex, varicella or zoster, cytomegalovirus as well as diseases caused by hepatitis B or Epstein-Barr viruses. The active compounds can also be used for the treatment or prophylaxis of papilloma or wart virus infections. In addition to their use in human medical therapy, the compounds of formula (I) can be administered to other animals for treatment or prophylaxis of viral diseases, e.g. in other mammals. For example, the active compounds are especially useful for the treatment of equine rhinopneumonitis.

The present invention also provides a method for the treatment or propylaxis of a viral disease in an animal, e.g. a mammal such as man, which comprises administering to the animal an effective antiviral amount of a compound of formula (I) or a pharmacologically acceptable salt thereof.

The active compounds may be administered by any route appropriate to the condition to be treated, suitable routes including oral, rectal, nasal, topical (including buccal and sublingual) vaginal and parenteral (including subcutaneous, intramuscular, intravenous, intradermal, intrathecal and epidural). It will be appreciated that the preferred route may vary with for example the condition of the recipient.

For each of the above-indicated utilities and indications the amount required of an active ingredient (as above defined) will depend upon a number of factors including the severity of the condition to be treated and the identity of the recipient and will ultimately be at the discretion of the attendant physician or veterinarian. In general however, for each of these utilities and indications, a suitable effective dose will be in the range 0.1 to 250 mg per kilogram bodyweight of recipient per day, preferably in the range 1 to 100 mg per kilogram bodyweight per day and most preferably in the range 5 to 20 mg per kilogram bodyweight per day; an optimum dose is about 10 mg per kilogram bodyweight per day. (Unless otherwise indicated, all weights of active ingredient are calculated as the parent compound of formula (I): for salts thereof the figures would be increased proportionately.) The desired dose is preferably presented as two, three, four or more sub-doses administered at appropriate intervals throughout the day. These sub-doses may be administered in unit dosage forms, for example, containing 10 to 1000 mg, preferably 20 to 500 mg and most preferably 100 to 400 mg of active ingredient per unit dosage form.

While it is possible for the active ingredients to be administered alone it is preferable to present them as pharmaceutical formulations. The formulations, both for veterinary and for human use, of the present invention comprise at least one active ingredient, as above defined, together with one or more acceptable carriers therefor and optionally other therapeutic ingredients. The carrier(s) must be "acceptable" in the sense of being compatible with the other ingredients of the formulation and not deleterious to the recipient thereof. The formulations include those suitable for oral, rectal, nasal, topical (including buccal and sublingual), vaginal or parenteral (including subcutanous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers of finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

For infections of the eye or other external tissues e.g. mouth and skin, the formulations are preferably applied as a topical ointment or cream containing the active ingredient in an amount of, for example, 0.075 to 20% w/w, preferably 0.2 to 15% w/w and most preferably 0.5 to 10% w/w. When formulated in an ointment, the active ingredients may be employed with either paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydoxyl groups such as propylene glycol, butane 1,3-diol, mannitol, sorbitol, glycerol and polyethylene glycol and mixtures thereof. The topical formulations may desirably include a compound which enhances absorption or penetration of the active ingredient through the skin or other affected areas. Examples of such dermal penetration enhancers include dimethylsulphoxide and related analogues.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavoured basis, usually sucrose and acacia or tragacanth; pastilles comprising the active ingredient in an inert basis such as gelatin and glycerine, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for nasal administration wherein the carrier is a solid include a coarse powder having a particle size for example in the range 20 to 500 microns which is administered in the manner in which snuff is taken, i.e. by rapid inhalation through the nasal passage from a container of powder held close up to the nose. Suitable formulations wherein the carrier is a liquid, for administration as for example a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described. Formulations for intramuscular administration are particularly preferred.

Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavouring agents.

The present invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

For oral administration the compositions can be in the form of a tablet, granule drench, paste, cachet, capsule or feed supplement. Granules may be made by the well known techniques of wet granulation, precompression or slugging. They can be administered to animals in an inert liquid vehicle so as to form a drench, or in a suspension with water or oil base. Preferably further accessory ingredients such as a dispensing agent are included. These formulations preferably contain from 15 to 85% of the active ingredient.

EXAMPLES

The following Examples illustrate the present invention. In the following Examples, XAD-2 designates an absorbent of polystyrene pearls. In the NMR spectra given the signals have been abbreviated as follows: s=singlet, d=doublet, t=triplet, q=quadruplet, m=multiplet, br s=broad signal.

EXAMPLE 1

Preparation of 9-(2-glycyloxyethoxymethyl)guanine hydrochloride (Formula I, wherein $R^3 = -COCH_2NH_2$. HCl).

(a) A solution of 0.84 ml (8.4 mmol) azidoacetyl chloride in 5 ml dry dimethylformamide was added dropwise over 10 minutes in an ice-cooled, thoroughly stirred suspension of 1.25 g (5.55 mmol) 9-(2-hydroxyethoxymethyl)guanine and 0.78 ml (5.55 mmol) triethylamine in 40 ml dry dimethylformamide. After 45 minutes of thorough stirring at 0° C., 0.11 ml (1.1 mmol) azidoacetylchloride in 1 ml dimethylformamide was added, and stirring was continued for 15 minutes. The reaction was stopped by the addition of 15 ml 7% NaHCO$_3$ solution whereupon the mixture was evaporated to dryness in vacuo. The residue was triturated with 20 ml of a mixture of methylene chloride:diethyl ether:ethanol (volume ratio 5:5:1). The solid substance obtained was filtered off, thoroughly washed with cold water and recrystallised from hot water, after treatment with active carbon. 1.02 g (62%) of 9-(2-azidoacetoxyethoxymethyl)guanine m.p. 175°–177° C. (decomposition) was obtained. MS m/e 308 (M$^{30}$), 151 (base+H); IR (KBr) 2110 (N$_3$), 1745 (COOR) cm$^{-1}$; UV (phosphate buffer, pH=7) $\lambda_{max}$ 253 nm ($\epsilon$ 8.42×10$^3$), 270 (sh); TLC R$_f$ 0.27 (CHCl$_3$—MeOH, 8:2), R$_f$ 0.60 (EtOH—HOAc, 8:2).

(b) A mixture of 1.23 g (4 mmol) of the product described in stage (a) 1.0 g 10% Pd/C and 4 ml 1.0N HCl in a 250 ml mixture of water and ethanol (volume ratio 1:1) was hydrogenated for 90 mins at a hydrogen pressure of 2.758 bar. The catalyst was then filtered off and thoroughly washed with water. The filtrate was combined with the wash water and evaporated to dryness in vacuo. The residue was twice crystallised from a mixture of water and ethanol to yield 0.83 g (65%) 9-(2-glycyloxyethoxymethyl)guanine hydrochloride with m.p. 148°–150° C. IR (KBr) 3200-2350 (NH$_3^+$), 1750 (COOR) cm$^{-1}$; UV (0.1N HCl). $\lambda_{max}$ 253 nm ($\epsilon$ 8.53×10$^3$), 275 (sh); NMR (60 MHz, DMSO-d$_6$/D$_2$O) $\delta$ 3.85 (s, 2H, N—CH$_2$—CO), 4.25 (m, 4H, —CH$_2$CH$_2$—), 5.5 (s, 2H, O—CH$_2$—N), 8.3 (s, 1H, 8—H); TLC R$_f$0.29 (EtOH—HOAc, 8:2);

Analysis: calculated for C$_{10}$H$_{14}$N$_6$O$_4$.HCl: C 37.69%, H 4.74%, N 26.87%. Found: C 37.84%, H 4.64%, N 26.25%).

EXAMPLE 2

Preparation of 9-(2-0-α-alanyloxyethoxymethyl)guanine hydrochloride (Formula I, wherein $R^3 = -COCH(CH_3)NH_2$. HCl).

(a) A mixture of 0.99 g (4 mmol) 9-(2-hydroxyethoxymethyl)guanine, 1.026 g (4.3 mmol) N-carbobenzyloxy-α-alanine (Aldrich), 0.04 g anhydrous p-toluene sulphonic acid and 1.755 g (5.6 mmol) N,N'-dicyclohexylcarbodiimide in 80 ml dry pyridine was stirred thoroughly for 1 day at room temperature. Subsequently 1 ml acetic acid was added and the mixture stirred thoroughly for a further hour. The reaction mixture was filtered off and the deposit thoroughly washed with hot methanol. The filtrate was combined with the wash liquid and evaporated dry, whereupon the residue was applied to a column of silica gel (50 g) and eluted with a mixture of chloroform:methanol (volume ratio 9:1). Crystallisation from methanol supplied 1.15 g (67%) of the protected α-alanine ester (Formula I, wherein $R^3 = -COCH(CH_3)$ NHCOOCH$_2$C$_6$H$_5$)m.p. 145°–147° C.

UV (MeOH) $\lambda_{max}$ 255 mm ($\epsilon$ 9.87×10$^3$, 270 (sh); TLC R$_f$0.40 (CHCl$_3$—MeOH, 8:2).

(b) A mixture of 0.662 g (1.54 mmol) of the protected-alanine ester obtained in stage (a) and 3.1 ml 0.5N HCl in a 200 ml mixture of water:methanol (volume ratio 1:1) was hydrogenated for 2 hours at a hydrogen pressure of 2.758 bar in the presence of 0.30 g 10% palladium on carbon. Thereafter the catalyst was filtered off and washed with water. The filtrate was combined with the wash water and evaporated to dryness in vacuo. The solid residue was crystallised from a mixture of water and ethanol to yield 0.354 g (71%) 9-(2-0-alanyloxyethoxymethyl)guanine-hydrochloride with m.p. 153°–155° C.

UV (0.1N HCl)$\lambda_{max}$ 254 nm ($\epsilon$ 1.10×10$^4$), 273 (sh); NMR (100 MHz, DMSO-d$_6$) 1.36 (d, 3H, CH$_3$, J=8 Hz), 3.72 (m, 2H, COOCH$_2$—CH$_2$—O), 4.04 (q, 1H, CH, J=8 Hz); 4.26 (m, 2H, COOCH$_2$—), 5.38 (s, 2H, O—CH$_2$—N), 6.74 (s, 2H, 2—NH$_2$), 7.84 (s, 1H, 8—H) 8.56 (br s, 3H, —NH$_3^+$), 10.9 (br s, 1H, 1—NH); TLC R$_f$ 0.23 (EtOH—HOAc, 8:2).

Analysis: calculated for C$_{11}$H$_{16}$O$_4$N$_6$.HCl: C 39.69%, H 5.15%, N 25.36%, Found: C 39.52%, H 5.06%, N 25.18%.

EXAMPLE 3

Preparation of 9-(2-0-$\beta$-alanyloxyethoxymethyl)guanine hydrochloride (Formula I, wherein R$^3$=—COCH$_2$CH$_2$NH$_2$.HCl).

(a) The method of Example 2(a) was repeated with 0.99 g (4 mmol) 9-(2-hydroxyethoxymethyl)guanine and 1.026 g (4.3 mmol) N-carbobenzyloxy-$\beta$-alanine (Aldrich). After crystallisation from methanol, this yielded 1.24 g (72%) of the protected $\beta$-alanine ester with m.p. 147°–148° C. UV $\lambda_{max}$ 254 nm ($\epsilon$ 9.91×10$^3$) (MeOH) 270 (sh) NMR (60 MHz, pyridine-d$_5$) $\delta$ 2.65 (t, 2H, —CH$_2$—COO, J=6 Hz), 3.65 (m, 4H, N—CH$_2$—CH$_2$ and COOCH$_2$—CH$_2$—O), 4.20 (m, 2H, COOCH$_2$—), 5.20 (s, 2H, O—CH$_2$—N), 5.50 (s, 2H, PhCH$_2$—O) 7.3 (m, 5H, phenyl), 8.1 (s, 1H, 8—H); TLC R$_f$ 0.41 (CHCl$_3$—MeOH, 8.2). (b) 0.99 g (2.3 mmol) of the protected $\beta$-alanine ester obtained in stage (a) was hydrogenated in an analogous manner to that of Example 2(b) in the presence of an equivalent quantity of HCl. After processing the reaction mixture in the manner of Example 2(b) 0.590 g (77%) of 9-(2-0-$\beta$-alanyloxyethoxymethyl)guanine hydrochloride with m.p. 202°–204° C. (decomposition) was obtained. UV (0.1N HCl) $\lambda_{max}$ 2.54 nm (1.09×10$^4$), 273 (sh); NMR (100 MHz, DMSO-d$_6$) $\delta$2.69 (m, 2H, —CH$_2$—COO), 3.01 (m, 2H, N—CH$_2$—CH$_2$), 3.71 (m, 2H, COOCH$_2$—CH$_2$—O), 4.15 (m, 2H, COOCH$_2$—), 5.38 (s, 2H, O—CH$_2$—N), 6.71 (s, 2H, 2—NH$_2$), 7.84 (s, 1H, 8—H), 8,08 (br s, 3H, —NH$_3^+$), 10.86 (br s, 1H, 1—NH), TLC R$_f$ 0.23 (EtOH—HOAc, 8:2);

Analysis: calculated for C$_{11}$H$_{16}$O$_4$N$_6$.HCl: C 39.69%, H 5.15%, N 25.36%. Found: C 39.78, H 5.23%, N 25.21%.

EXAMPLE A

Eye Drop Formulation

An eye drop formulation was prepared by dissolving a compound of any of Examples 1-3 in a concentration of 1% (weight/vol) in an isotonic buffer solution which contained 1.52 g boric acid, 0.0008 g borax and 0.01 g benzalkonium chloride per 100 ml distilled water. The pH of the solution was 5.7.

Biological Activity (a) Antiviral Activity in vitro

In a series of biological tests an investigation was made of the activity of the compounds of Examples 1-3 in comparison with acyclovir against various viruses in cell cultures of primary rabbit kidney cells.

The viruses used were: herpes simplex type 1 (strains KOS, Mc Intyre and F) and herpes simplex type 2 (strains Lyons, G and 196).

The origin of the six herpes simplex strains and the method for the measurement of the retardation of the cytopathogenicity induced by the virus are described by E. de Clercq et al. in J. Infect Dis., 141, 563 (1980).

The results of the tests are reproduced in the following table, where they are expressed in the minimum inhibitory concentration, that is to say the concentration (in $\mu$g/ml) which is necessary to reduce by 50% the cytopathogenicity induced by the virus in the cell culture. In all cases average values of 2 or 3 separate determinations are given.

The abbreviations used are:

HSV-1: herpes simplex virus, Type 1
HSV-2: herpes simplex virus, Type 2.

TABLE

| Compound (Example No:) | Minimum Inhibitory Concentration ($\mu$g/ml) | | | | | |
|---|---|---|---|---|---|---|
| | HSV-1 (KOS) | HSV-1 (McIntyre) | HSV-1 (F) | HSV-2 (Lyons) | HSCV-2 (G) | HSV-2 (196) |
| 1 | 0.1 | 0.1 | 0.1 | 0.04 | 0.08 | 0.07 |
| 2 | 0.4 | 0.4 | 0.4 | 0.07 | 0.2 | 0.1 |
| 3 | 0.2 | 0.4 | 0.5 | 0.1 | 0.15 | 0.1 |
| Acyclovir | 0.08 | 0.1 | 0.09 | 0.04 | 0.06 | 0.06 |

The table shows that the antiviral activity of the compounds of Examples 1 to 3 is substantially that of 9-(2-hydroxyethoxymethyl)guanine.

(b) Antiviral Activity in vivo

The in vivo antiviral activity of the compound of Example 1 was compared with the known antiviral bromovinyldeoxyuridine.

Eye drops containing 0.5% (w/v) of bromovinyldeoxyuridine or 1% w/v of compound of Example 1 were prepared in an isotonic borate buffer containing 1.52 g boric acid, 0.008 g borax and 0.01 g benzalkoniumchloride in 100 ml distilled water. The pH of the solution was 5.7. The vehicle alone without any antiviral ingredients was used as placebo. The eye drops were coded.

A cross-breed of California albino and Dendermonde white rabbits, weighing between 1.5 and 2 kg, were used.

Thirty rabbits were used to produce stromal keratitis according to the technique of McNeill and Kaufman (Arch. Ophthalmol. 97: 727–729, 1979). Rabbits were anesthetized by a subcutaneous injection of fentanyl citrate at 1 ml/kg. A 0.2 ml virus suspension, containing 10$^{4.5}$ plaque-forming units of HSV-1 (strain McIntyre) per ml, was injected into the central corneal stroma of both eyes.

The rabbits were numbered serially and allocated at random to three groups of the rabbits each. Treatment consisted of administration of eye drops containing the compound of Example 1, bromovinyldeoxyuridine, or placebo eye drops. Treatment was started one day after virus inoculation. One drop of the eye drop formulation was instiled into the eye at hourly intervals, nine times as day. Therapy was continued for 5 consecutive days. Both eyes of each rabbit received the same modification.

Keratitis evaluation

The severity of keratitis was evaluated daily by the same person using a slitlamp. White illumination was used to examine the corneal stroma and anterior chamber structures. One percent fluorescein sodium eye drops and a cobalt blue filter were employed to judge epithelial keratitis and corneal ulceration.

Results

The compound of Example 1 and bromovinyldeoxyuridine eye drops were effective in suppressing stromal keratitis. The differences in the keratitis score between the placebo group and the two active compounds were statistically significant throughout the whole observation period. Severe keratitis developed in the placebo group within the first few days post-infection. The compound of Example 1 prevented the progression of stromal disease, so that the mean keratitis scores remained nearly constant once treatment with the drug was initiated. Bromovinyldeoxy uridine caused a gradual healing of stromal keratitis. The beneficial effect of bromovinyldeoxyuridine became significantly better than that of the compound of Example 1 from the fourth treatment day onwards.

Stromal HSV-1 keratitis in the experiment was accompanied by iritis. The severity of this complicating iritis followed the same pattern as the keratitis scores. Thus, both compounds caused a significant reduction in the iritis scores. The differences in the iritis scores between the placebo and the compound of Example 1 groups were significant from day 2 till day 8. Significant differences were also noted between the iritis scores of the placebo and bromovinyldeoxyuridine groups.

We claim:
1. 9-(2-0-Glycyloxyethoxymethyl)guanine.
2. 9-(2-0-$\alpha$-Alanyloxyethoxymethyl)guanine.
3. 9-(2-0-$\beta$-Alanyloxyethoxymethyl)guanine.
4. A pharmacologically acceptable salt of 9-(2-0-Glycyloxyethoxymethyl)guanine.
5. The hydrochloride salt of claim 4.
6. The method of treating a keratitis infection in a mammal which comprises administering the compound or salt of claim 1, 4 or 5 to said mammal.
7. The method of treating an iritis infection in a mammal which comprises administering the compound or salt of claim 1, 4 or 5 to said mammal.
8. A pharmacologically acceptable salt of claim 2 or 3.

* * * * *